United States Patent
Gupta et al.

(10) Patent No.: US 9,567,335 B2
(45) Date of Patent: Feb. 14, 2017

(54) PROCESS FOR SODIUM SALT OF (2S, 5R)-2-CARBOXAMIDO-7-OXO-6-SULFOOXY-1,6-DIAZA-BICYCLO[3.2.1]OCTANE

(71) Applicant: WOCKHARDT LIMITED, Aurangabad (IN)

(72) Inventors: Sunil Vishnubhagwan Gupta, Kota (IN); Sunil Bhaginath Jadhav, Ahmednagar (IN); Vipul Rane, Aurangabad (IN); Prasad Keshav Deshpande, Aurangabad (IN); Satish Bhawsar, Aurangabad (IN); Ravindra Dattatraya Yeole, Aurangabad (IN); Mahesh Vithalbhai Patel, Aurangabad (IN)

(73) Assignee: WOCKHARDT LIMITED, Bandra East, Mumbai (IN)

( * ) Notice: Subject to any disclaimer, the term of this patent is extended or adjusted under 35 U.S.C. 154(b) by 0 days.

(21) Appl. No.: 14/770,231

(22) PCT Filed: Oct. 12, 2013

(86) PCT No.: PCT/IB2013/059325
§ 371 (c)(1),
(2) Date: Aug. 25, 2015

(87) PCT Pub. No.: WO2014/135930
PCT Pub. Date: Sep. 12, 2014

(65) Prior Publication Data
US 2016/0016955 A1    Jan. 21, 2016

(30) Foreign Application Priority Data
Mar. 8, 2013 (IN) .......................... 718/MUM/2013

(51) Int. Cl.
*C07D 471/08* (2006.01)

(52) U.S. Cl.
CPC .................................. *C07D 471/08* (2013.01)

(58) Field of Classification Search
CPC ................................................... C07D 471/08
(Continued)

(56) References Cited

U.S. PATENT DOCUMENTS 7,112,592 B2 * 9/2006 Lampilas ............. C07D 487/08
514/300
2008/0255358 A1 * 10/2008 Bamford ............. C07D 471/04
544/333

(Continued)

FOREIGN PATENT DOCUMENTS

| EP | 2657234 | * 10/2013 |
| WO | WO2009091856 | * 7/2009 |
| WO | WO2012086241 | * 6/2012 |

OTHER PUBLICATIONS

Valeur; Chem. Soc. Rev., 2009, 38, 606-631.*

*Primary Examiner* — Noble Jarrell
*Assistant Examiner* — Daniel Carcanague
(74) *Attorney, Agent, or Firm* — Bio Intellectual Property Services LLC (Bio IPS); O. (Sam) Zaghmout

(57) ABSTRACT

A process for preparation of a sodium salt of (2S,5R)-2-carboxamido-7-oxo-6-sulfooxy-1,6-diaza-bicyclo[3.2.1]octane is disclosed which is comprising the amidation of a compound of Formula (II) to obtain a compound of Formula (III).

(Continued)

X-Ray Diffractogram

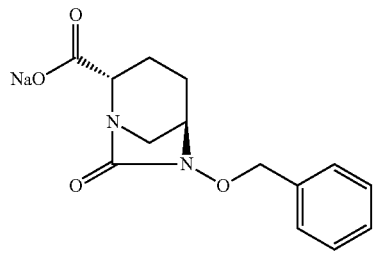

(II)

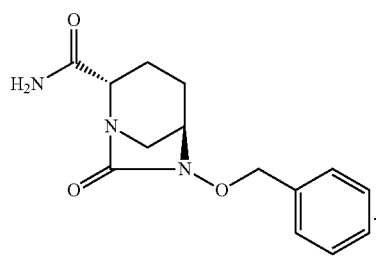

(III)

(58) Field of Classification Search
USPC .......................................................... 546/121
See application file for complete search history.

(56) References Cited

U.S. PATENT DOCUMENTS

| | | | |
|---|---|---|---|
| 2011/0152311 A1* | 6/2011 | Dedhiya | C07D 471/08 514/300 |
| 2012/0165533 A1* | 6/2012 | Abe | C07D 471/08 546/121 |
| 2012/0323010 A1* | 12/2012 | Ronsheim | C07D 211/60 546/121 |
| 2014/0296526 A1* | 10/2014 | Patil | C07D 471/08 546/121 |
| 2016/0002233 A1* | 1/2016 | Wankhede | C07D 471/08 546/121 |
| 2016/0002234 A1* | 1/2016 | Pawar | C07D 471/08 546/121 |
| 2016/0002235 A1* | 1/2016 | Joshi | C07D 471/08 546/121 |
| 2016/0002236 A1* | 1/2016 | Deshmukh | C07D 471/08 546/121 |

7 Claims, 1 Drawing Sheet

* cited by examiner

X-Ray Diffractogram
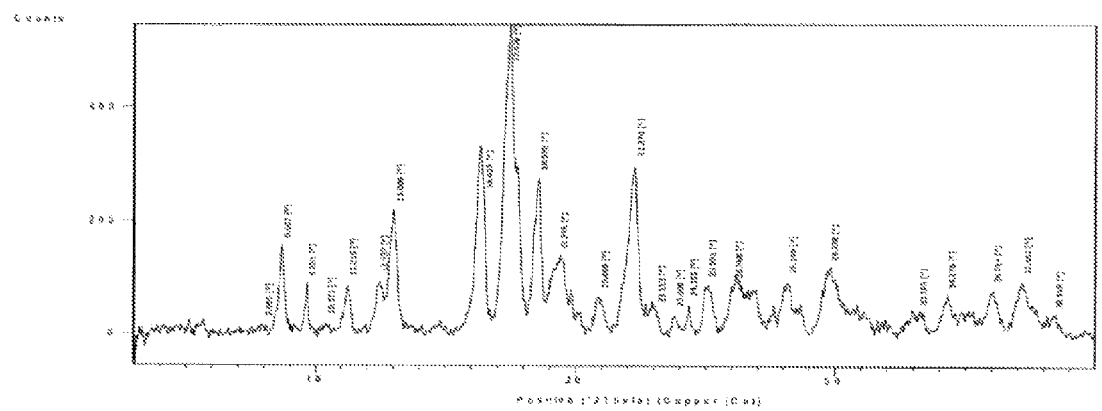

PROCESS FOR SODIUM SALT OF (2S, 5R)-2-CARBOXAMIDO-7-OXO-6-SULFOOXY-1,6-DIAZA-BICYCLO[3.2.1]OCTANE

RELATED PATENT APPLICATIONS

This application claims benefit of Indian Patent Application No. 718/MUM/2013 filed on Mar. 8, 2013, the disclosures of which are incorporated herein by reference in its entirety as if fully rewritten herein. All references including patents, patent applications, and literature cited in the specification are expressly incorporated herein by reference in their entirety.

FIELD OF THE INVENTION

The invention relates to a process for preparation of a sodium salt of (2S,5R)-2-carboxamido-7-oxo-6-sulfooxy-1,6-diaza-bicyclo[3.2.1]octane.

BACKGROUND OF THE INVENTION

A compound of Formula (I), chemically known as a sodium salt of (2S,5R)-2-carboxamido-7-oxo-6-sulfooxy-1,6-diaza-bicyclo[3.2.1]octane has antibacterial properties. The compound of Formula (I) is also known as Avibactam or NXL-104 and is disclosed in U.S. Pat. No. 7,112,592.

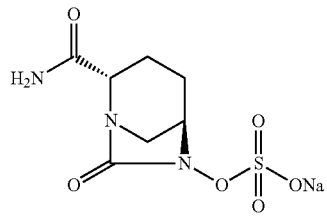

Formula (I)

SUMMARY OF THE INVENTION

In one general aspect, there is provided a process for preparation of a compound of Formula (I), comprising:

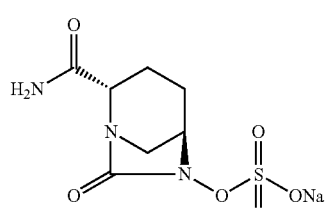

Formula (I)

(a) reacting a compound of Formula (II) with an amidating agent to obtain a compound of Formula (III);

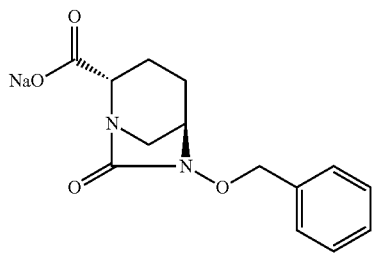

Formula (II)

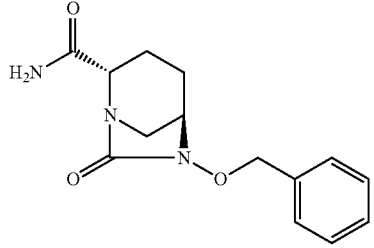

Formula (III)

(b) hydrogenolysis of a compound of Formula (III) to obtain a compound of Formula (IV);

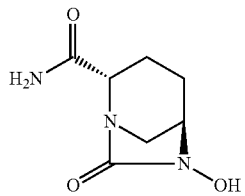

Formula (IV)

(c) sulfonating a compound of Formula (IV) to obtain a compound of Formula (V); and

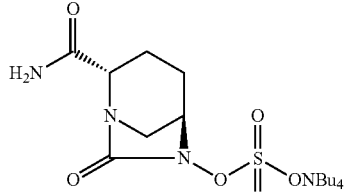

Formula (V)

(d) converting a compound of Formula (V) into a compound of Formula (I).

The details of one or more embodiments of the invention are set forth in the description below. Other features, objects and advantages of the invention will be apparent from the following description including claims.

DETAILED DESCRIPTION OF THE INVENTION

Reference will now be made to the exemplary embodiments, and specific language will be used herein to describe the same. It should nevertheless be understood that no limitation of the scope of the invention is thereby intended. Alterations and further modifications of the inventive features illustrated herein, and additional applications of the principles of the invention as illustrated herein, which would occur to one skilled in the relevant art and having possession of this disclosure, are to be considered within the scope of the invention. It must be noted that, as used in this specification and the appended claims, the singular forms "a," "an," and "the" include plural referents unless the content clearly dictates otherwise. All references including patents, patent applications, and literature cited in the specification are expressly incorporated herein by reference in their entirety as if fully rewritten herein.

The term "HOBt" as used herein refers to 1-hydroxybenzotriazole.

The term "EDC" as used herein refers to 1-ethyl-3-(3-dimethylaminopropyl) carbodiimide.

In one general aspect, there is provided a process for preparation of a compound of Formula (I), comprising:

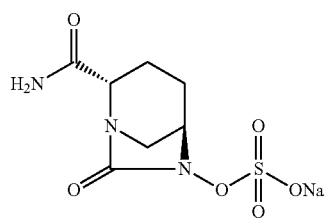

Formula (I)

(a) reacting a compound of Formula (II) with an amidating agent to obtain a compound of Formula (III);

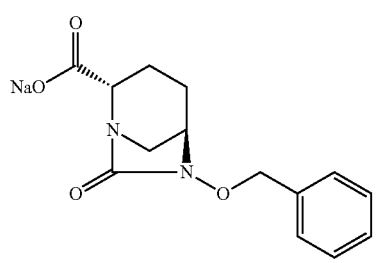

Formula (II)

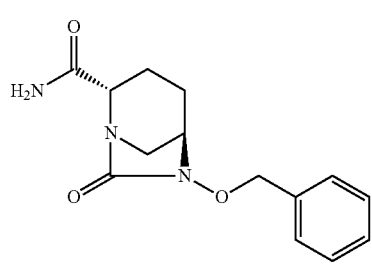

Formula (III)

(b) hydrogenolysis of a compound of Formula (III) to obtain a compound of Formula (IV);

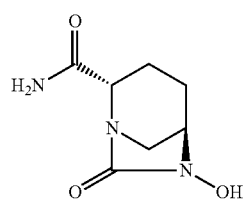

Formula (IV)

(c) sulfonating a compound of Formula (IV) to obtain a compound of Formula (V); and

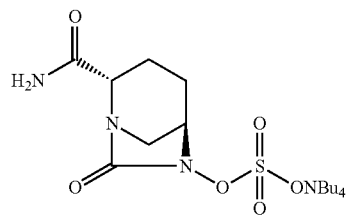

Formula (V)

(d) converting a compound of Formula (V) into a compound of Formula (I).

The compound of Formula (III) is obtained by reacting a compound of Formula (II) with a suitable amidating agent. In some embodiments, the amidating agent comprises 1-ethyl-3-(3-dimethylaminopropyl)carbodiimide and 1-hydroxybenzotriazole:ammonia complex. In some other embodiments, the compound of Formula (III) is obtained by reacting a compound of Formula (II) with 1-hydroxybenzotriazole:ammonia complex in presence of 1-ethyl-3-(3-dimethylaminopropyl)carbodiimide hydrochloride and 1-hydroxybenzotriazole. The amidation reaction may be carried out in a suitable solvent. In some embodiments, the amidation reaction is carried out in water as a reaction solvent. In some embodiments, a compound of Formula (III) was obtained by reacting a compound of Formula (II) with 1-ethyl-3-(3-dimethylaminopropyl)carbodiimide hydrochloride and 1-hydroxybenzotriazole in presence of ammonia solution.

The compound of Formula (IV) is obtained by hydrogenolysis of a compound of Formula (III). The hydrogenolysis reaction can be carried out using a suitable hydrogenolysis agent. In some embodiments, hydrogenolysis of a compound of Formula (III) to obtain a compound of Formula (IV) is carried out in presence of a transition metal catalyst and hydrogen source. In some other embodiments, the transition metal catalyst is palladium on carbon and hydrogen source is hydrogen gas. In some other embodiments, the hydrogenolysis reaction is carried out in presence of a suitable solvent such as, for example, a mixture of N,N-dimethyl formamide and dichloromethane (1:1 v/v). In some embodiments, the hydrogenolysis of a compound of Formula (III) to obtain a compound of Formula (IV) is carried out using 10% palladium on carbon catalyst, in presence of hydrogen gas in N,N-dimethylformamide:dichloromethane mixture as a solvent (1:1 v/v).

The compound of Formula (V) is obtained by sulfonating a compound of Formula (IV). The sulfonation reaction can be carried out in presence of a suitable solvent. In some embodiments, the sulfonation of a compound of Formula (IV) to obtain a compound of Formula (V) is carried out by reacting a compound of Formula (IV) with sulfur trioxide-N,N-dimethylformamide complex, followed by treatment with 10% aqueous tetrabutyl ammonium acetate.

The compound of Formula (V) is converted to a compound of Formula (I) in presence of a suitable reagent. In some embodiments, the compound of Formula (V) is converted to a compound of Formula (I) by reacting a compound of Formula (V) with sodium-2-ethyl-hexanoate.

In some embodiments, the compound of Formula (I) is prepared using a process described in Scheme 1.

In another general aspect, the process according to the invention results in the preparation of a compound of Formula (I) having a purity of at least 97% as determined by HPLC.

In some embodiments, there is provided a compound of Formula (I), having an X-ray powder diffraction pattern comprising a peak selected from the group consisting of 8.69 (±0.2), 9.65 (±0.2), 11.22 (±0.2), 12.44 (±0.2), 13.01 (±0.2), 16.48 (±0.2), 17.48 (±0.2), 18.58 (±0.2), 19.35 (±0.2), 20.89 (±0.2), 22.27 (±0.2), 25.03 (±0.2), 26.07 (±0.2), 28.14 (±0.2), 29.74 (±0.2), 34.28 (±0.2), 36.01 (±0.2), and 37.18 (±0.2) degrees 2 theta.

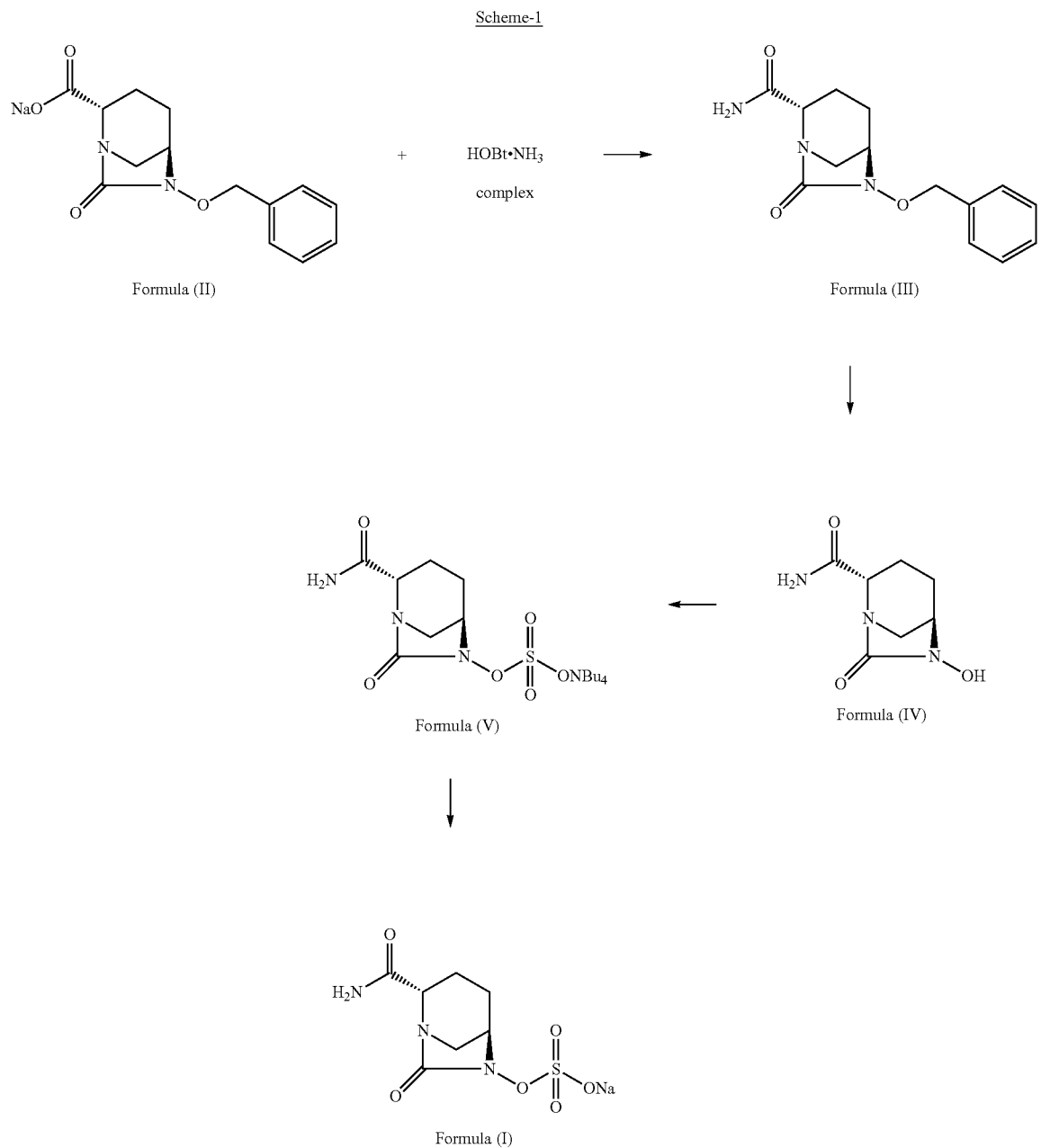

In some embodiments, the compound of Formula (I) has an X-ray powder diffraction pattern substantially the same as shown in FIG. 1.

It will be readily apparent to one skilled in the art that varying substitutions and modifications may be made to the invention disclosed herein without departing from the scope and spirit of the invention. For example, those skilled in the art will recognize that the invention may be practiced using a variety of different compounds within the described generic descriptions.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example-1

Preparation of sodium salt of (2S,5R)-sulfuric acid mono-{2-carboxamido-7-oxo-1,6-diaza-bicyclo [3.2.1]octane Step-1: Preparation of (2S,5R)-2-Carboxamido-6-benzyloxy-7-oxo-1,6-diaza-bicyclo[3.2.1]octane Method-1:

The starting compound ((2S,5R)-sodium 6-benzyloxy-7-oxo-1,6-diaza-bicyclo[3.2.1] octane-2-carboxylate; compound of Formula (II)) was prepared according to a procedure disclosed in Indian Patent Application No. 699/MUM/2013. To a 100 ml round bottom flask equipped with magnetic stirrer was charged (2S,5R)-sodium 6-benzyloxy-7-oxo-1,6-diaza-bicyclo[3.2.1]octane-2-carboxylate (10.0 gm, 0.033 mol), followed by freshly prepared HOBt. ammonia complex (10.0 gm, 0.066 mol), EDC hydrochloride (9.62 gm, 0.050 mol) and 1-hydroxy benzotriazole (4.51 gm, 0.033 mol). To this mixture of solids, water (30 ml) was added at about 35° C., and stirring was started. Precipitation occurred after 30 minutes. The reaction mixture was stirred for additional 20 hours at about 35° C. Dichloromethane (150 ml) was added to the suspension and the reaction mass was allowed to stir for 10 minutes. The layers were separated. Aqueous layer was washed with additional dichloromethane (50 ml). Combined organic layer was evaporated under vacuum to provide a residue (21 gm). The residue was stirred with acetone (21 ml) for 30 minutes and filtered under suction to provide (2S,5R)-2-carboxamido-6-benzyloxy-7-oxo-1,6-diaza-bicyclo[3.2.1]octane as a white solid in 5.5 gm quantity in 60% yield after drying under vacuum at about 45° C.

Analysis

H$^1$NMR (DMSO-d$_6$)

7.35-7.45 (m, 6H), 7.25 (bs, 1H), 4.89-4.96 (dd, 2H), 3.68 (d, 1H), 3.62 (s, 1H), 2.90 (s, 2H), 2.04-2.07 (m, 1H), 1.70-1.83 (m, 1H), 1.61-1.66 (m, 2H).

MS (ES+) $C_{14}H_{17}N_3O_3$=276.1 (M+1)

Purity: 93.95% as determined by HPLC

Specific rotation: $[\alpha]^{25}_D$–8.51° (c 0.5%, CHCl$_3$)

Method-2:

Alternatively, the above compound was prepared by using the following process. To a 50 ml round bottom flask equipped with magnetic stirrer was charged a solution of (2S,5R)-sodium 6-benzyloxy-7-oxo-1,6-diaza-bicyclo [3.2.1]octane-2-carboxylate (1 gm, 0.003 mol) in water (15 ml) followed by EDC hydrochloride (1 gm, 0.005 mol) and 1-hydroxybenzotriazole (0.39 gm, 0.003 mol) at 35° C. under stirring. The reaction mass was stirred for 1 hour to obtain a white suspension. At this point, aqueous ammonia was added (2 ml, 40% w/v), under stirring. The reaction mixture was stirred for additional 5 hours. The suspension was filtered, washed with additional water (10 ml) to provide (2S,5R)-2-carboxamido-6-benzyloxy-7-oxo-1,6-diaza-bicyclo[3.2.1] after drying under vacuum at 45° C. in 0.21 gm quantity.

Step-2: Preparation of Tetrabutyl Ammonium Salt of (2S,5R)-2-carboxamido-6-sulfooxy-7-oxo-1,6-diaza-bicyclo[3.2.1]octane To a Parr shaker bottle, was charged (2S,5R)-2-carboxamido-6-benzyloxy-7-oxo-1,6-diaza-bicyclo[3.2.1]octane (7.0 gm, 0.025 mol) followed by a 1:1 mixture of N,N-dimethylformamide and dichloromethane (35 ml: 35 ml). To the clear solution was added 10% palladium on carbon (1.75 gm) and hydrogen pressure was applied up to 50 psi. The suspension was shaken for 3 hours at 35° C. The catalyst was removed by filtering the reaction mixture over celite bed. The catalyst bed was washed with dichloromethane (30 ml). Combined filtrate was evaporated under vacuum at a temperature below 40° C. to obtain an oily residue. The oily residue (4.72 gm) was dissolved in N,N-dimethylformamide (35 ml) and to the clear solution was added sulfur trioxide. DMF complex at 10° C. under stirring in one lot. The mixture was allowed to stir at 35° C. for additional 2 hours. As TLC showed complete conversion, 10% aqueous solution of tetrabutyl ammonium acetate (9.44 gm, 0.031 mol, in 30 ml water) was added under stirring and the reaction mixture was stirred for overnight and then subjected to high vacuum distillation on rotavapor by not exceeding temperature above 40° C. to obtain a residue. Xylene (50 ml) was added to the residue and similarly evaporated to remove traces of DMF. The dry residue thus obtained was stirred with water (70 ml) and extracted with dichloromethane (70 ml×2). Combined organic extract was dried over sodium sulfate and solvent was evaporated under vacuum below 40° C. to obtain oily residue in 7 gm quantity as a crude product. It was stirred with methyl isobutyl ketone (21 ml) for 30 minutes at about 35° C. to obtain a white solid in 5.9 gm quantity as a tetrabutyl ammonium salt of (2S,5R)-2-carboxamido-6-sulfooxy-7-oxo-1,6-diaza-bicyclo[3.2.1]octane in pure form in 46% yield.

Analysis

NMR: (CDCl$_3$)

6.63 (s, 1H), 5.48 (s, 1H), 4.34 (br s, 1H), 3.90 (d, 1H), 3.27-3.40 (m, 9H), 2.84 (d, 1H), 2.38 (dd, 1H), 2.21-2.20 (m, 1H), 1.60-1.71 (m, 12H), 1.40-1.50 (m, 8H), 1.00 (t, 12H).

MS (ES–) C7H10N3O6S. N(C4H9)4=264.0 (M–1) as a free sulfonic acid.

Purity: 98.98% as determined by HPLC.

Specific rotation: $[\alpha]^{25}_D$–30.99° (c 0.5%, MeOH)

Step-3: Synthesis of Sodium Salt of (2S,5R)-2-carboxamido-6-sulfooxy-7-oxo-1,6-diaza-bicyclo[3.2.1]octane To a 100 ml round bottom flask equipped with magnetic stirrer was charged tetrabutyl ammonium salt of (2S,5R)-2-carboxamido-6-sulfooxy-7-oxo-1,6-diaza-bicyclo[3.2.1]octane (5.5 gm, 0.0108 mol) followed by ethanol (28 ml) to provide a clear solution under stirring at about 35° C. To the reaction mixture was added a solution of sodium 2-ethyl hexanoate (3.6 gm, 0.021 mol) dissolved in ethanol (28 ml) in one lot under stirring to provide precipitation. The suspension was stirred for additional 2 hours to effect complete precipitation at about 35° C. The reaction mixture was filtered under suction and the wet cake was washed with acetone (30 ml×2). The wet cake was dried at 40° C. under vacuum to provide sodium salt of (2S,5R)-2-carboxamido-6-sulfooxy-7-oxo-1,6-diaza-bicyclo[3.2.1]octane as a white solid in 2.6 gm quantity in 83% yield.

Analysis $H^1$NMR (DMSO-$d_6$)

7.39 (s, 1H), 7.24 (s, 1H), 3.98 (s, 1H), 3.68 (d, 1H), 3.02 (d, 1H), 2.92 (d, 1H), 2.00-2.10 (m, 1H), 2.80-2.90 (m, 1H), 1.55-1.70 (m, 2H).

MS (ES−) C7H10N3O6SNa=264.0 (M−1) as a free sulfonic acid;

Purity: 97.98% as determined by HPLC

Specific rotation: $[\alpha]^{25}_D$ −49.37° (c 0.5%, water)

Powder X-ray diffractogram: (degrees 2 theta):

8.69 (±0.2), 9.65 (±0.2), 11.22 (±0.2), 12.44 (±0.2), 13.01 (±0.2), 16.48 (±0.2), 17.48 (±0.2), 18.58 (±0.2), 19.35 (±0.2), 20.89 (±0.2), 22.27 (±0.2), 25.03 (±0.2), 26.07 (±0.2), 28.14 (±0.2), 29.74 (±0.2), 34.28 (±0.2), 36.01 (±0.2), and 37.18 (±0.2).

Typical X-ray analysis was performed as follows. Pass the test substance through sieve #100 BSS or gently grind it with a mortar and pestle. Place the test substance uniformly on a sample holder having cavity surface on one side, press the sample and cut into thin uniform film using a glass slide in such a way that the surface of the sample should be smooth and even. Record the X-ray diffractogram using the following instrument parameters.

Instrument: X-Ray Diffractometer (PANalytical, Model X'Pert Pro MPD)
Target source: Cu k (α)
Anti-scattering slit (Incident beam): 1°
Programmable Divergent slit: 10 mm (fixed)
Anti-scattering slit (Diffracted beam): 5.5 mm
Step width: 0.02°
Voltage: 40 kV
Current: 40 mA
Time per step: 30 seconds
Scan range: 3 to 40°

We claim:

1. A process for preparation of a compound of Formula (I), comprising:

Formula (I)

(a) reacting a compound of Formula (II) with 1-hydroxybenzotriazole-ammonia complex in the presence of water as a solvent to obtain a compound of Formula (III);

Formula (II)

Formula (III)

(b) hydrogenolysis of the compound of Formula (III) to obtain a compound of Formula (IV);

Formula (IV)

(c) sulfonating the compound of Formula (IV) to obtain a compound of Formula (V); and Formula (V)

(d) converting the compound of Formula (V) into the compound of Formula (I).

2. The process according to claim 1, wherein the compound of Formula (II) is converted to the compound of Formula (III) in the presence of 1-ethyl-3-(3-dimethylaminopropyl)carbodiimide and 1-hydroxybenzotriazole.

3. The process according to claim 1, wherein the hydrogenolysis of the compound of Formula (III) to obtain the compound of Formula (IV) is carried out in the presence of a transition metal catalyst and a hydrogen source.

4. The process according to claim 3, wherein the transition metal catalyst is palladium on carbon and the hydrogen source is hydrogen gas.

5. The process according to claim 3 or 4, wherein the hydrogenolysis of the compound of Formula (III) to obtain the compound of Formula (IV) is carried out in the presence of N,N-dimethylformamide and dichloromethane (1:1 v/v) as a reaction solvent.

6. The process according to claim 1, wherein the sulfonating of the compound of Formula (IV) to obtain the compound of Formula (V) is carried out by reacting the compound of Formula (IV) with sulfur trioxide-N,N-dimethyl formamide complex, followed by treatment with 10% aqueous tetrabutyl ammonium acetate.

7. The process according to claim 1, wherein the compound of Formula (V) is converted to the compound of Formula (I) by reacting the compound of Formula (V) with sodium-2-ethyl-hexanoate.

* * * * *